United States Patent [19]
Berg et al.

[11] Patent Number: 5,256,259
[45] Date of Patent: Oct. 26, 1993

[54] SEPARATION OF HEXANE FROM VINYL ACETATE BY AZEOTROPIC DISTILLATION

[75] Inventors: Lloyd Berg; Randi W. Wytcherley, both of Bozeman, Mont.

[73] Assignee: Lloyd Berg, Bozeman, Mont.

[21] Appl. No.: 38,497

[22] Filed: Mar. 29, 1993

[51] Int. Cl.$^5$ .......................... B01D 3/36; C07C 7/08; C07C 67/54
[52] U.S. Cl. ........................................ 203/57; 203/60; 203/62; 203/63; 203/DIG. 10; 560/248; 585/860; 585/862; 585/864; 585/866
[58] Field of Search ........................ 203/57, 62, 63, 60, 203/DIG. 10; 560/248; 585/860, 862, 864, 866

[56] References Cited

U.S. PATENT DOCUMENTS

| | | | |
|---|---|---|---|
| 3,394,057 | 7/1968 | Miller et al. | 560/248 |
| 3,691,021 | 9/1972 | Feldman et al. | 203/65 |
| 3,736,236 | 5/1973 | Di Fiore et al. | 203/DIG. 10 |
| 4,897,161 | 1/1990 | Berg et al. | 203/56 |
| 4,925,533 | 5/1990 | Berg | 203/DIG. 10 |
| 5,106,460 | 4/1992 | Berg | 203/60 |

*Primary Examiner*—Wilbur Bascomb, Jr.

[57] ABSTRACT

Hexane cannot be separated from vinyl acetate by conventional distillation or rectification because of the minimum boiling azeotrope. Hexane can be readily separated from vinyl acetate by using azeotropic distillation. Typical examples of effective agents are acetone, acetonitrile or methyl t-butyl ether.

2 Claims, No Drawings

SEPARATION OF HEXANE FROM VINYL ACETATE BY AZEOTROPIC DISTILLATION

FIELD OF THE INVENTION

This invention relates to a method for separating hexane from vinyl acetate using certain organic compounds as the agents in azeotropic distillation.

DESCRIPTION OF PRIOR ART

Azeotropic distillation is the method of separating close boiling compounds or azeotropes from each other by carrying out the distillation in a multiplate rectification column in the presence of an added liquid, said liquid forming an azeotrope with one or both of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agents is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

Hexane, B. P.=69° C. and vinyl acetate, B. P.=72.7° C. form a minimum azeotrope boiling at 57° C. and containing about 62% hexane and therefore are impossible to separate by distillation or rectification. Azeotropic distillation would be an attractive method to break this azeotrope and separate hexane from vinyl acetate by rectification.

TABLE 1

| Theoretical and Actual Plates Required vs. Relative Volatility for Hexane - Vinyl Acetate Separation | | |
| --- | --- | --- |
| Relative Volatility | Theoretical Plates Required At Total Reflux, 95% purity | Actual Plates Required 75% Efficiency |
| 1.2 | 33 | 44 |
| 1.25 | 27 | 36 |
| 1.30 | 23 | 31 |
| 1.40 | 18 | 24 |
| 1.60 | 13 | 17 |

The advantage of using azeotropic distillation in this separation can be seen from the data shown in Table 1. If an agent can be found that will increase the relative volatility to 1.6, only seventeen actual plates are required for 95% purity.

OBJECTIVE OF THE INVENTION

The object of this invention is to provide a process or method of azeotropic distillation that will enhance the relative volatility of hexane to vinyl acetate in their separation in a rectification column. It is a further object of this invention to identify certain organic compounds which are effective as azeotropic distillation agents, that are stable and can be readily separated from hexane and vinyl acetate and can be recycled to the azeotropic distillation column with little decomposition.

SUMMARY OF THE INVENTION

The objects of the invention are provided by a process for the separation of hexane from vinyl acetate which entails the use of certain organic compounds as the agent in azeotropic distillation.

DETAILED DESCRIPTION OF THE INVENTION

We have discovered that certain organic compounds will effectively increase the relative volatility between hexane and vinyl acetate by rectification when employed as the agent in azeotropic distillation.

TABLE 2

| Effective Azeotropic Formers To Separate Hexane From Vinyl Acetate | |
| --- | --- |
| Compounds | Relative Volatility |
| Acetone | 1.55 |
| Methanol | 1.35 |
| Acetonitrile | 1.50 |
| Methyl acetate | 1.28 |
| Ethyl formate | 1.23 |
| Methyl t-butyl ether | 1.17* |

*Brings out the vinyl acetate as overhead

Table 2 summarizes the data obtained with these agents in a rectification column. The agents which are effective are acetone, methanol, acetonitrile, methyl acetate ethyl formate and methyl t-butyl ether.

THE USEFULNESS OF THE INVENTION

The usefulness or utility of this invention can be demonstrated by referring to the data presented in Tables 1 and 2. All of the successful agents show that hexane can be separated from vinyl acetate by means of azeotropic distillation in a rectification column and that the ease of separation as measured by relative volatility is considerable.

WORKING EXAMPLES

Example 1

One hundred grams of the hexane—vinyl acetate azeotrope and fifty grams of acetone were charged to a glass perforated plate rectification column containing 7.3 theoretical plates. After four hours at total reflux, overhead and bottoms samples were taken and analyzed by gas chromatography. The overhead was 96.9% hexane, 3.1% vinyl acetate; the bottoms was 55.6% hexane, 44.4% vinyl acetate which is a relative volatility of 1.55.

Example 2

One hundred grams of the hexane—vinyl acetate azeotrope and 100 grams of methyl t-butyl ether were charged to the glass perforated plate rectification column containing 7.3 theoretical plates. After six hours at total reflux, overhead and bottoms samples were taken and analyzed. The overhead was 53.1% hexane, 21.9% vinyl acetate and 25% methyl t-butyl ether; the bottoms was 88.3% hexane, 11.7% vinyl acetate, 0% methyl t-butyl ether. This indicates a relative volatility of vinyl acetate to hexane of 1.17.

We claim:

1. A method for recovering hexane from a mixture of hexane and vinyl acetate which comprises distilling a mixture of hexane and vinyl acetate in the presence of an azeotrope forming agent, recovering the hexane and the azeotrope forming agent as overhead product and obtaining the vinyl acetate from the stillpot, wherein said azeotrope forming agent comprises a material selected from the group consisting of acetone, methanol, acetonitrile, methyl acetate, ethyl formate and nitromethane.

2. A method for recovering vinyl acetate from a mixture of vinyl acetate and hexane which comprises distilling a mixture of vinyl acetate and hexane in the presence of an azeotrope forming agent, recovering the vinyl acetate and the azeotrope forming agent as overhead product and obtaining the hexane from the stillpot, wherein said azeotrope forming agent is methyl t-butyl ether.

* * * * *